US007816359B2

(12) United States Patent
Loiseleur et al.

(10) Patent No.: US 7,816,359 B2
(45) Date of Patent: Oct. 19, 2010

(54) N-PHENYL-2-PYRIMIDINE-AMINE DERIVATIVES

(75) Inventors: Olivier Loiseleur, Saint-Louis (FR); Daniel Kaufmann, Therwil (CH); Stephan Abel, Weil am Rhein (DE); Hans Michael Bürger, Allschwil (CH); Mark Meisenbach, Durmenach (FR); Beat Schmitz, Allschwil (CH); Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/845,934

(22) Filed: Aug. 28, 2007

(65) Prior Publication Data
US 2007/0293504 A1    Dec. 20, 2007

Related U.S. Application Data

(62) Division of application No. 10/503,538, filed as application No. PCT/EP03/01188 on Feb. 6, 2003, now Pat. No. 7,456,283.

(30) Foreign Application Priority Data
Feb. 7, 2002   (GB)   .................................. 0202873.6

(51) Int. Cl.
A61K 31/497    (2006.01)
A61K 31/505    (2006.01)
A01N 43/54     (2006.01)
(52) U.S. Cl. .................................. 514/252.12; 514/275
(58) Field of Classification Search ................. 514/275, 514/252.12
See application file for complete search history.

(56) References Cited
U.S. PATENT DOCUMENTS

| 2,808,433 | A | 10/1957 | Struve |
| 3,505,389 | A | 4/1970 | Weil et al. |
| 3,763,234 | A | 10/1973 | Brill |
| 4,281,000 | A | 7/1981 | Dusza et al. |
| 4,623,486 | A | 11/1986 | Lombardino et al. |
| 4,816,485 | A | 3/1989 | Satzinger et al. |
| 5,137,918 | A | 8/1992 | Weiershausen et al. |
| 5,521,184 | A | 5/1996 | Zimmermann |
| 2005/0159391 | A1 | 7/2005 | Ding et al. ..................... 514/80 |

FOREIGN PATENT DOCUMENTS

| DE | 531480 | 7/1931 |
| DE | 44 28 380 | 2/1996 |
| EP | 0 564 409 | 10/1993 |
| GB | 862127 | 3/1961 |
| JP | 49087761 | 8/1974 |
| JP | 50129738 | 4/1975 |
| JP | 56065804 | 11/1979 |
| JP | 3130252 | 6/1990 |
| JP | 2001510192 | 7/1997 |
| WO | 92 17066 | 10/1992 |
| WO | 99 03854 | 1/1999 |
| WO | WO 99/03854 | * 1/1999 |
| WO | WO9959959 | 11/1999 |
| WO | 00 18738 | 4/2000 |
| WO | WO0027820 | 5/2000 |
| WO | 01 27089 | 4/2001 |

OTHER PUBLICATIONS

Basha et al., "A mild, general method for conversion of esters to amides," Tetrahedron Letters, No. 48, pp. 4171-4173 (1977).
Database Crossfire Beilstein, Online, Beilstein Institute zur Foerderung der Chemischen Wissenschaften, Frankfurt am Main, DE (1961), Database accession No. 2775102.
Database Crossfire Beilstein, Online, Beilstein Institute zur Foerderung der Chemischen Wissenschaften, Frankfurt am Main, DE (1970), Database accession No. 3005098.
Database Crossfire Beilstein Online, Beilstein Institut zur Foerderung der Chemischen Wissenschaften, Frankfurt am Main, DE (1957), Database accession No. 3401828.
Database Crossfire Beilstein Online, Beilstein Institut zur Foerderung der Chemischen Wissenschaften, Frankfurt am Main, DE (1931), Database accession No. 3411040.
Lipton, M.F. et al., "Conversion of Esters to Amides with Dimethylaluminum Amides: N,N-Dimethylcyclohexanecarboxamide," Organic Synthesis, John Wiley 1979, vol. 59, pp. 49-53 (1979).
Gless, R.D., "Lewis Acid Mediated Aminolysis of Esters: Conversion of Methyl (S)-(-)-2-Chloropropionate to (S)-(+)-N,N-Diethyl-2-Chloropropionamide," vol. 16(6), pp. 633-638 (1986).
Levin et al., "An Alternative Procedure for the Aluminum-Mediated Conversion of Esters to Amides," Synthetic Communications, vol. 12(13), pp. 989-993 (1982).
Matsumoto et al., "Direct Aminolysis of Nonactivated and Thermally Unstable Esters at High Pressure," Chem. Ber., vol. 122, pp. 1357-1363 (1989).
Beckwith, A.L.J., "Synthesis of Amides," University of Adelaide, (1970).
Larock, Richard C., ed., "Comprehensive Organic Transformations—A guide to Functional Group Preparations," pp. 156-160, pp. 1777-1779, 2388-2392, 5186-5189, 4873-4876 (1989).
Paquette, Leo A., Editor-in-Chief, Encyclopedia of Reagents for Organic Synthesis, vol. 1, A—Bru, The Ohio State University, Columbus, OH (1995).
Ludovici, D W., et al., "Evolution of Anti-HIV Drug Candidates. Part 3: Diarylpyrimidine (DAPY) Analogues", Bioorganic & Medicinal Chemistry Letters, 11 (2001), pp. 2235-2239.
Moffat et al. "4-pyridin-5-yl, etc." Bioorganic & Medicinal Chemistry Letters 9 (1999) 3351-3356.

* cited by examiner

Primary Examiner—James O Wilson
Assistant Examiner—Erich A Leeser
(74) Attorney, Agent, or Firm—George R. Dohmann

(57) ABSTRACT

The present invention relates to novel amides and a process for preparing these amides.

3 Claims, No Drawings

N-PHENYL-2-PYRIMIDINE-AMINE DERIVATIVES

This application is a divisional of U.S. application Ser. No. 10/503,538, filed Jan. 20, 2005, which is a 371 of International Application No. PCT/EP03/01188, filed Feb. 6, 2003.

The present invention provides novel amides, a process for preparing these amides and the use of these amides.

In particular, the present invention provides novel amides of formula I

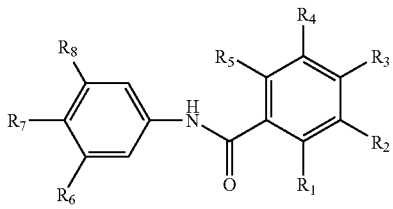

wherein one of the radicals $R_1$, $R_2$, $R_3$, $R_4$ and $R_5$ is a) a radical selected from the group consisting of lower alkyl, amino; mono- or di-lower alkylamino; lower alkanoylamino; lower alkoxy-carbonyl; and lower alkyl which is substituted by amino, mono- or di-lower alkylamino or lower alkanoylamino, or b) an unsubstituted or substituted radical selected from the group consisting of benzylamino; benzoylamino; pyrrolidinyl; piperidyl; piperazinyl; piperazinyl-carbonyl; morpholinyl, thiomorpholinyl; and lower alkyl substituted by benzylamino, benzoylamino, halogen, pyrrolidinyl, piperidyl, piperazinyl, e.g. 4-methyl-piperazinyl-, thiomorpholinyl, or morpholinyl, the substituents of said substituted radical being selected from the group consisting of cyano; lower alkyl; hydroxy- or amino-substituted lower alkyl; trifluoromethyl; free, etherified or esterified hydroxy; lower alkoxy; lower alkanoyloxy; free, alkylated or acylated amino; mono- or di-lower alkylamino; lower alkanoylamino; benzoylamino; free or esterified carboxy; lower alkoxycarbonyl and halogen, and the other four radicals are independently hydrogen, cyano; lower alkyl; hydroxy- or amino-substituted lower alkyl; trifluoromethyl; free, etherified or esterified hydroxy; lower alkoxy; lower alkanoyloxy; free, alkylated or acylated amino; mono- or di-lower alkylamino; lower alkanoylamino; benzoylamino; free or esterified carboxy; lower alkoxycarbonyl and halogen;

or $R_1$ and $R_2$, $R_2$ and $R_3$, $R_3$ and $R_4$, or $R_4$ and $R_5$ together are a substituted or unsubstituted alkylene radical having 4 carbon atoms, the substituents preferably being selected from cyano, unsubstituted or hydroxy-, amino- or 4-methyl-piperazinyl-substituted lower alkyl, such as especially methyl, trifluoromethyl, free, etherified or esterified hydroxy, free, alkylated or acylated amino and free or esterified carboxy;

and the other three radicals are independently hydrogen, cyano; lower alkyl; hydroxy- or amino-substituted lower alkyl; trifluoromethyl; free, etherified or esterified hydroxy; lower alkoxy; lower alkanoyloxy; free, alkylated or acylated amino; mono- or di-lower alkylamino; lower alkanoylamino; benzoylamino; free or esterified carboxy; lower alkoxycarbonyl and halogen;

and one of the radicals $R_6$, $R_7$ and $R_8$ is halogen, $NH_2$, $NO_2$, $NHC(O)CF_3$, $NHC(O)CH_3$, $NHC(NH)NH_2$, and the other two radicals are independently hydrogen, lower alkyl, lower fluorinated alkyl, benzyl or phenyl;

or a salt or crystal form thereof.

Compounds of formula I may be in the form of a salt preferably a pharmaceutically acceptable salt.

Such salts are formed, for example, as acid addition salts, preferably with organic or inorganic acids, from compounds of formula I or IV with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, oxalic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

Preferred salts of formula I, are chloride, bromide, mesylate, acetate, trifluoroacetate.

The term "lower" within the scope of this application denotes radicals having up to and including 7, preferably up to and including 4 carbon atoms, preferably methyl or ethyl.

The term "lower fluorinated alkyl" within the scope of this application denotes radicals having up to and including 7, preferably up to and including 4 carbon atoms, preferably methyl or ethyl, which are substituted by fluorine such as mono, di or trifluoro-methyl, trifluoro-ethyl.

The term "piperazinyl" within the scope of this application denotes unsubstituted piperazinyl or N-lower alkyl-piperazinyl such as 4-methyl-piperazinyl-.

Halogen is especially fluorine, chlorine, bromine, or iodine, especially fluorine, chlorine, or bromine.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkylamino, such as dimethylamino. Acylated amino is, for example, lower alkanoylamino or benzoylamino.

Esterified carboxy is, for example, lower alkoxycarbonyl, such as methoxycarbonyl.

Preferably, $R_3$ is lower alkyl substituted by benzylamino, benzoylamino, halogen, pyrrolidinyl, piperidyl, piperazinyl, e.g. 4-methyl-piperazinyl-, or morpholinyl, thiomorpholinyl, the substituents of said substituted radical being selected from the group consisting of cyano; lower alkyl; hydroxy- or amino-substituted lower alkyl; trifluoromethyl; free, etherified or esterified hydroxy; lower alkoxy; lower alkanoyloxy; free, alkylated or acylated amino; mono- or di-lower alkylamino; lower alkanoylamino; benzoylamino; free or esterified carboxy; lower alkoxycarbonyl and halogen.

Preferably, $R_3$ is lower alkyl substituted by pyrrolidinyl, piperidyl, piperazinyl, e.g. 4-methyl-piperazinyl-, or morpholinyl, thiomorpholinyl, the substituents of said substituted radical being selected from the group consisting of lower alkyl; hydroxy- or amino-substituted lower alkyl;

Preferably, $R_1$, $R_2$, $R_4$, $R_5$ and $R_8$ are hydrogen.

Preferably, $R_7$ is lower alkyl such as methyl or fluorinated alkyl such as trifluoromethyl.

Most preferably, $R_3$ is (4-methyl-piperazinyl)-methyl, $R_1$, $R_2$, $R_4$, $R_5$ and $R_8$ are hydrogen, $R_6$ is halogen, $NH_2$, $NO_2$, $NHC(O)CF_3$, $NHC(O)CH_3$, $NHC(NH)NH_2$, and $R_7$ is methyl.

Amides of formula I may be prepared by a process as depicted below:

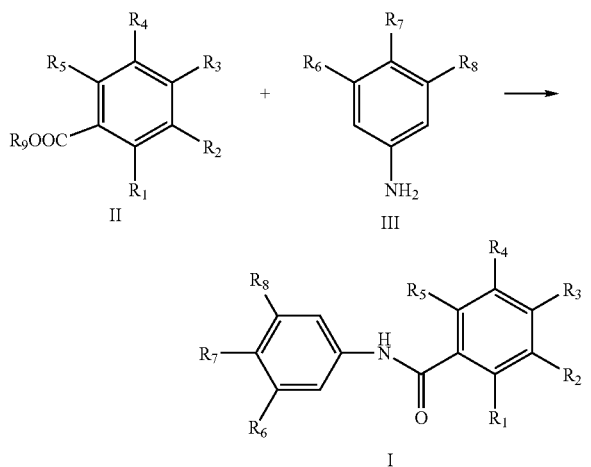

wherein $R_1$ to $R_8$ are as defined above and $R_9$ is hydrogen, methyl, ethyl or aryl.

However, direct conversion of unactivated carboxylic acids or esters to amides, such as compounds of formula II, with amines is difficult and typically requires high reaction temperature, e.g. of about 200° C., or use of strong bases, such as sodium methoxide, sodium amide, n-butyl lithium, sodium hydride or Grignard reagent. Thus there is a need for a more efficient amidation process as hitherto known.

The present Applicants have found that direct conversion of unactivated carboxylic acids or esters of compounds of formula II with compounds of formula III to amides of formula I may successfully be conducted under mild conditions A) where $R_9$ is methyl, ethyl or aryl:
  in the presence of
  1) a Lewis acid,
  2) an aprotic organic solvent, and optionally
  3) a base,
  at a temperature of between 20° C. and 80° C., preferably at about 40° C., for a period of between 1 hour and 1 day, preferably 8 hours, preferably under inert atmosphere, preferably at atmospheric pressure, and hydrolysis of the resulting product; or B) where $R_9$ is hydrogen:
  in the presence of
  1) thionylchloride,
  2) an aprotic organic solvent, and optionally
  3) a base,
  at a temperature of between 20° C. and 70° C., preferably 45° C., for a period of between 1 hour and 1 day, preferably 6 hours, preferably under inert atmosphere, preferably at atmospheric pressure.

Thus, the present invention provides in another aspect processes for the preparation of a compound of formula I by reacting compounds of formula II with compounds of formula III A) where $R_9$ is methyl, ethyl or aryl:
  in the presence of
  1) a Lewis acid,
  2) an aprotic organic solvent, and optionally
  3) a base
  at a temperature of between 20° C. and 80° C., preferably at about 40° C., for a period of between 1 hour and 1 day, preferably 8 hours, preferably under inert atmosphere, preferably at atmospheric pressure, and the resulting product is hydrolyzed; or B) where $R_9$ is hydrogen:
  in the presence of
  1) thionylchloride,
  2) an aprotic organic solvent, and optionally
  3) a base,
  at a temperature of between 20° C. and 70° C., preferably 45° C., for a period of between 1 hour and 1 day, preferably 6 hours, preferably under inert atmosphere, preferably at atmospheric pressure.

Suitable Lewis acids for process A) include Al(lower alkyl)$_3$ (e.g. $AlMe_3$, $AlEt_3$, $Al(iBu)_3$), $AlCl_3$, $AlBr_3$, $EtAlCl_2$, $MeAlCl_2$, $Me_2AlCl$, $Et_2AlCl$ and the corresponding sesquichlorides. Preferably, the Lewis acid is selected from $AlCl_3$, $EtAlCl_2$ or $Et_2AlCl$, even more preferably is $AlCl_3$. Typically, the Lewis acid is present in an amount of 1 to 4 mole equivalents. In the case of $AlMe_3$, $AlEt_3$, and $Al(iBu)_3$, e.g. 2 to 3 mole equivalents, preferably about 2.5 mole equivalents are present; in the case of $AlCl_3$, $AlBr_3$, $EtAlCl_2$, $MeAlCl_2$, $Me_2AlCl$, $Et_2AlCl$ and the corresponding sesquichlorides, preferably 1.5 to 3.5, preferably 2.5 mole equivalents are present.

Thionylchloride is preferably present in process B) in an amount of 1.5 to 10 mole equivalents, preferably 1.5 mole equivalents.

Suitable aprotic organic solvents for carrying out process A) and B) include toluene/acetonitrile, toluene, benzene, chlorobenzene, dichlorobenzene, acetonitrile, mesitylene and pyridine.

A preferred base for process A) or B) is N,N-diisopropylethylamine, lutidine, pyridine, or tertiary amines.

In an alternative aspect, the present invention provides a process for the preparation of compounds of formula I by reacting compounds of formula V with compounds of formula $R_{14}$—H

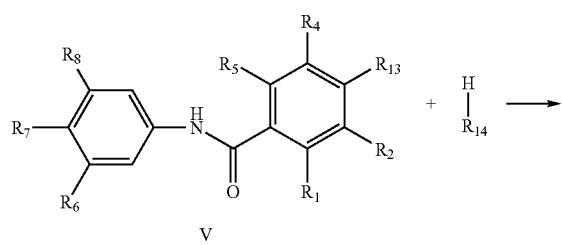

wherein,
$R_{13}$ is a lower alkyl substituted by a halogen,
$R_{14}$ is benzylamino, benzoylamino, pyrrolidinyl, piperidyl, piperazinyl, optionally substituted by radicals being selected from the group consisting of cyano; lower alkyl; hydroxy- or amino-substituted lower alkyl,
$R_3$ is a lower alkyl substituted by benzylamino, benzoylamino, pyrrolidinyl, piperidyl, piperazinyl, optionally substituted by radicals being selected from the group consisting of cyano; lower alkyl; hydroxy- or amino-substituted lower alkyl.

The reaction is preferably carried out in the presence of an organic solvents, such as THF (Tetrahydrofuran) or directly in the amine solution $R_{14}$—H.

Preferably piperazinyl is a N-lower-alkylpiperazine e.g. N-methylpiperazine.

Preferably, $R_1$, $R_2$, $R_4$ and $R_5$ are independently hydrogen, cyano; lower alkyl; hydroxy- or amino-substituted lower alkyl; trifluoromethyl; free, etherified or esterified hydroxy; lower alkoxy; lower alkanoyloxy; free, alkylated or acylated amino; mono- or di-lower alkylamino; lower alkanoylamino; benzoylamino; free or esterified carboxy; lower alkoxycarbonyl and halogen.

Compounds of formula V can be obtained by reacting compounds of formula II' with compounds of formula III,

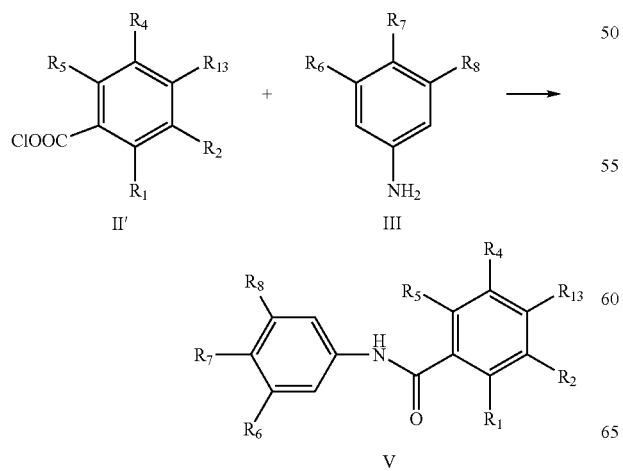

In the presence of
1) an organic solvent such as THF (Tetrahydrofuran)
2) a base such as N,N-diisopropylethylamine, lutidine, pyridine, or tertiary amines.

Alternatively, $R_{14}$—H is directly added in the reactional medium without further purification in order to react with the resulting compound of formula V.

THF can be used alone or in mixtures with other solvents to increase overall solvent power.

The amides of formula I may be formed and isolated from the reaction mixture, e.g. as conventional, e.g. by removal of solvent from the reaction mixture, e.g. by concentration such as evaporation, e.g. to dryness or almost dryness, e.g. until crystallization or precipitation of an amide of formula I occurs; or by extraction, e.g. as a salt, or into another solvent which may be the same or different from that used in the amidation; and precipitation or crystallization of an amide of formula I. The amides of formula I may be purified by conventional techniques such as recrystallization or chromatography.

Compounds of formula II or II' may be prepared by methods known to the skilled person in the art. Compounds of formula III are commercially available e.g. from Fluka, Aldrich or Acros or may be prepared by methods known to the skilled person in the art.

The compounds of formula I may be used for the preparation of compounds of formula IV,

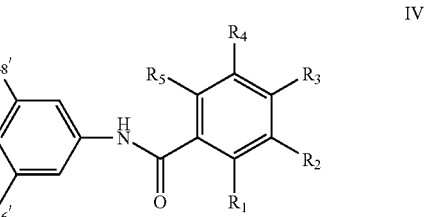

wherein $R_1$ to $R_5$ are as defined above and
one of the radicals $R_6'$, $R_7'$ and $R_8'$ is

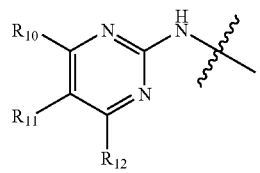

wherein $R_{10}$ is 4-pyperazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, and $R_{11}$ and $R_{12}$ are each independently of the other hydrogen or lower alkyl and the other two radicals are independently hydrogen, lower alkyl, e.g. methyl, benzyl or phenyl;

or a pharmaceutically acceptable salt or crystal form thereof.

Compounds of formula IV may be in the form of a salt, preferably a pharmaceutically acceptable salt, as described above.

Preferred salts are for example chloride, bromide, mesylate, acetate, trifluoroacetate.

Compounds of formula IV inhibit the tyrosine kinase activity of the receptor for the epidermal growth factor (EGF) and are useful, inter alia, for the treatment of benign or malignant tumors. They are able to effect tumour regression and to prevent metastatic spread and the growth of micrometastases. In particular, they can be used for treating epidermal hyperproliferation (psoriasis), for treating neoplasms of epithelial character, e.g. mastocarcinoma, and leucemia. In addition, the compounds of formula IV are useful for treating diseases of the immune system and inflammations, subject to the involvement of protein kinases. The compounds of formula IV may also be used for treating diseases of the central or peripheral nervous system, subject to the involvement of signal transmission by protein kinases.

Thus, in another aspect the present invention provides a process for the preparation of compounds of formula IV from compounds of formula I and the use of compounds of formula I for the preparation of compounds of formula IV wherein $R_1$ to $R_8$' are as herein described.

This invention relates to a process for the preparation of a compound of formula IV or a pharmaceutically acceptable salt or crystal form thereof, by reacting a compound of formula I as described herein, with a compound of formula VII

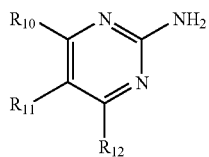

VII wherein $R_{10}$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom e.g. 3-pyridyl and unsubstituted or substituted at the nitrogen atom by oxygen, and $R_{11}$ and $R_{12}$ are each independently of the other hydrogen or lower alkyl, by conventional methods.

Preferably in a first step, the compound of formula I is prepared from compounds of formula II and III as described herein.

The present invention also relates to a process for the preparation of a compound of formula IV or a pharmaceutically acceptable salt or crystal form thereof,
by reacting a compound of formula I as described herein, wherein the radical $R_6$ is —NHC(NH)$NH_2$,
with a compound of formula VI

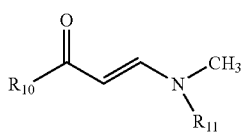

VI wherein $R_{10}$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom e.g. 3-pyridyl and unsubstituted or substituted at the nitrogen atom by oxygen, and $R_{11}$ is hydrogen or lower alkyl;

by conventional methods.

Preferably the reaction is carried out in a polar organic solvent such as n-butanol.

Preferably $R_{10}$ is 3-pyridyl and $R_{11}$ is methyl.

In one embodiment, a compound of formula I wherein $R_6$ is NHC(NH)$NH_2$, $R_7$ is methyl and $R_8$ is hydrogen may e.g. be treated with 3-dimethylamino-1-(3-pyridyl)-2-propen-1-one to a compound of formula IV wherein $R_6$' is 4-(3-pyridyl)-2-pyrimidinamino, $R_7$' is methyl and $R_8$' is hydrogen, corresponding to the compound of formula IV as described in example 21 of EP 564 409. A compound of formula I wherein $R_6$ is Br, $R_7$ is methyl and $R_8$ is hydrogen may e.g. be treated with 4-(3-pyridyl)-2-pyrimidine-amine, e.g. as available from Chempacific, in the presence of Pd(0) or Pd(II) in the presence of a phosphine ligand to give compound of formula IV wherein $R_6$' is 4-(3-pyridyl)-2-pyrimidinamino, $R_7$' is methyl and $R_8$' is hydrogen.

In another embodiment, compounds of formula I wherein $R_6$ is $NO_2$, $R_7$ is methyl and $R_8$ is hydrogen may e.g. be transformed to a compound of formula I wherein $R_6$ is $NH_2$, $R_7$ is methyl and $R_8$ is hydrogen using standard methods known to the skilled person. Compounds of formula I wherein $R_6$ is halogen, NHC(O)$CF_3$ or NHC(O)$CH_3$, preferably Br, $R_7$ is methyl and $R_8$ is hydrogen may e.g. be transformed to a compound wherein $R_6$ is $NH_2$, $R_7$ is methyl and $R_8$ is hydrogen using standard methods known to the skilled person. Compounds of formula I wherein $R_6$ is $NH_2$, $R_7$ is methyl and $R_8$ is hydrogen may e.g. be transformed to a compound of formula I wherein $R_6$ is NHC(NH)$NH_2$, $R_7$ is methyl and $R_8$ is hydrogen.

Accordingly, the present invention provides a process for the preparation of compounds of formula IV wherein in a first step a compound of formula I is prepared from compounds of formula II and III as hereinabove described, preferably in the presence of $AlCl_3$, Al(lower alkyl)$_3$ e.g. $AlMe_3$, $AlEt_3$, Al(iBu)$_3$ or $SOCl_2$, and in a second step the compound of formula I is reacted to a compound of formula IV by conventional methods. Preferably, said process is provided for preparation of a compound of formula IV wherein $R_1$, $R_2$, $R_4$, $R_5$ and $R_8$' are hydrogen, $R_3$ is (4-methyl-piperazinyl)-methyl, $R_6$' is 4-(3-pyridyl)-2-pyrimidinamino, and $R_7$' is methyl.

The processes of the present invention allow the synthesis of compounds of formula IV, preferably a compound of formula IV wherein $R_1$, $R_2$, $R_4$, $R_5$ and $R_8$' are hydrogen, $R_3$ is (4-methyl-piperazinyl)-methyl, $R_6$' is 4-(3-pyridyl)-2-pyrimidinamino, and $R_7$' is methyl, in a more efficient and higher yielding manner than previously described in the literature e.g. in EP 564409. No expensive coupling reagents have to be used. The higher throughput combined with less steps as in the prior art will result in significantly lower production costs In the previously described syntheses, mutagenic intermediates may be formed. In the processes of the present invention all intermediates show a negative AMES Test (a specific test for mutagenicity; performed according to the OECD Guideline for Testing of Chemicals, 471: Bacterial Reverse Mutation Test, Adopted Jul. 21, 1997) which is a strong indication that no mutagenic intermediates are formed which would be a significant improvement of occupational health. Furthermore, these processes allow the synthesis of e.g. radiolabeled compounds.

Following is a description by way of example only of the process of the present invention.

| | | |
|---|---|---|
| AlMe₃ | trimethylaluminium | from FLUKA |
| Al(iBu)₃ | triisobutylaluminium | from FLUKA |
| AlCl₃ | aluminium trichloride | from Merck |
| platinum on sulfide carbon | | from Acros |
| thionyl chloride | | from FLUKA |
| Celite Filter Cel | | from FLUKA |
| Rochelle Salt | potassium-sodium tartrate | from FLUKA |
| platinum on carbon | | from Engelhardt |
| cyanamide | | from FLUKA |
| 3-dimethylamino-1-pyridin-3-yl-propenone | | from FLUKA |
| sodium-tert,-butylate | | from FLUKA |
| rac-BINAP | 2,2'-bis-(diphenylphosphino)-1,1'-binaphthalin | synthesized according to literature procedure |
| Pd₂(dba)₃*CHCl₃ | tris(dibenzylideneacetone)-dipalladium chloroform complex | from FLUKA |

Preference is given above all especially to the compound of formula IV which is N-{5-[4-(4-methyl-piperazino-methyl)-benzoylamido]-2-methylphenyl}-4-(3-pyridyl)-2-pyrimidine-amine. N-{5-[4-(4-methyl-piperazino-methyl)-benzoylamido]-2-methylphenyl}-4-(3-pyridyl)-2-pyrimidine-amine (also known as "Imatinib" [International Nonproprietary Name]) and the use thereof, especially as an antitumour agent, are described in Example 21 of European patent application EP-A-0 564 409, which was published on 6 Oct. 1993, and in equivalent applications and patents in numerous other countries, e.g. in U.S. Pat. No. 5,521,184 and in Japanese patent 2706682. Another preference is given to the β-crystal form of 4-(4-methylpiperazin-1-ylmethyl)-N-[4-methyl-3-(4-pyridin-3-yl)pyrimidin-2-ylamino)phenyl]-benzamide methanesulfonate as described in the European patent application No. 998 473 published on May 10, 2000. The term "4-(4-methylpiperazin-1-ylmethyl)-N-[4-methyl-3-(4-pyridin-3-yl)pyrimidin-2-yl-amino)phenyl]-benzamide" includes the β-crystal form as described in the European patent application No. 998 473.

Very preferably a compound of formula IV is in the form of a pharmaceutically acceptable salt, especially in the form of its monomesylate salt.

The compounds of formula IV are generically and specifically disclosed in the patent applications EP 0 564 409 A1 and WO 99/03854, in particular in the compound claims and the final products of the working examples, the subject-matter of the final products, the pharmaceutical preparations and the claims are hereby incorporated into the present application by reference to these publications. Comprised are likewise the corresponding stereoisomers as well as the corresponding polymorphs, e.g. crystal modifications, which are disclosed therein.

Thus in a further aspect this invention relates to the use of compounds of formula I for the synthesis of compounds of formula IV, especially 4-(4-methylpiperazin-1-ylmethyl)-N-[4-methyl-3-(4-pyridin-3-yl)pyrimidin-2-ylamino)phenyl]-benzamide or a pharmaceutically acceptable salt thereof or crystal form thereof.

Furthermore, this invention also relates to a pharmaceutical composition comprising, a) one or more pharmaceutically acceptable excipients,
b) at least one pharmaceutically active compound of formula IV, and
c) between 0.00001% and 5% by weight of at least one compound of formula I, preferably between 0.00001% and 0.1%, most preferably between 0.0001% and 0.1%.

The present invention particularly relates to pharmaceutical compositions especially tablets comprising 4-(4-methylpiperazin-1-ylmethyl)-N-[4-methyl-3-(4-pyridin-3-yl)pyrimidin-2-ylamino)phenyl]-benzamide or a pharmaceutically acceptable salt or crystal form thereof.

Preferably c) is a compound of formula I wherein, $R_3$ is (4-methyl-piperazinyl)-methyl, $R_1$, $R_2$, $R_4$, $R_5$ and $R_8$ are hydrogen, $R_6$ is Br, Cl, $NH_2$, $NO_2$, $NHC(O)CF_3$, $NHC(O)CH_3$ or $NHC(NH)NH_2$, and $R_7$ is methyl, or a salt thereof.

One or more pharmaceutically acceptable excipients may be present in the composition, e.g. those conventionally used, e.g. (1.1) at least one binder, e.g. microcrystalline cellulose, hydroxypropylmethyl cellulose, (1.2) at least one disintegrant, e.g. cross-linked polyvinylpyrrolidinone, e.g. Crospovidone®, (1.3) at least one glidant, e.g. colloidal silicon dioxide, (1.4) at least one lubricant, e.g. magnesium stearate and/or (1.5) basic coating. In the tablet according to the present invention, microcrystalline cellulose is used as a binder.

EXAMPLE A

Capsules with Imatinib (4-[(4-methyl-1-piperazin-1-ylmethyl)-N-[4-methyl-3-[4-(3-pyridinyl)-2-pyrimidinyl]amino]phenyl]benzamide) Methanesulfonate of Formula IV, β-crystal Form Capsules containing 119.5 mg of the compound named in the title (=SALT I) corresponding to 100 mg of Imatinib (free base) as active substance are prepared in the following composition. The composition containing also compounds of formula I wherein, $R_3$ is (4-methyl-piperazinyl)-methyl, $R_1$, $R_2$, $R_4$, $R_5$ and $R_8$ are hydrogen, $R_6$ is Br, Cl, $NH_2$, $NO_2$, $NHC(O)CF_3$, $NHC(O)CH_3$, $NHC(NH)NH_2$, and $R_7$ is methyl.

| Composition | |
|---|---|
| SALT I | 119.5 mg |
| Compounds of formula I | 0.0005 mg |
| Cellulose MK GR | 92 mg |
| Crospovidone XL | 15 mg |
| Aerosil 200 | 2 mg |
| Magnesium stearate | 1.5 mg |
| | 230.0005 mg |

The capsules are prepared by mixing the components and filling the mixture into hard gelatin capsules, size 1.

EXAMPLE 1

Preparation of N-(4-Methyl-3-bromo-phenyl)-4-(4-methyl-piperazin-1-ylmethyl)-benzamide A solution of trimethylaluminium (2M in toluene, 15.0 ml) is added over a period of 30 min to a solution of 3-bromo-4-methyl-aniline (2.15 g, 11.5 mmol) and 4-(4-methyl-piperazin-1-ylmethyl)-benzoic acid methyl ester (2.87 g, 11.5 mmol) in toluene (20 ml) at 40° C. under an atmosphere of argon. After gas evolution ceases, the reaction mixture is stirred 30 min before being cooled to 0° C. and partitioned between cold aqueous 1N NaOH (100 ml) and toluene (100 ml). The organic layer is extracted with aqueous saturated NH$_4$Cl (100 ml) and aqueous saturated NaCl (100 ml) The organic layer is concentrated in vacuo to give 4.69 g (97 area % by HPLC) of the title compound as pale yellow crystals.

4-(4-Methyl-piperazin-1-ylmethyl)-benzoic acid methyl ester is obtained as follows:

A solution of 4-formyl-benzoic acid methyl ester (10.0 g, 61 mmol) in methanol (100 ml) is treated sequentially with 1-methylpiperazine (6.7 g, 67 mmol) and platinum (5%) on sulfided carbon (0.5 g). The resulting solution is then heated at 90° C. and is subjected to a pressure of 5 bar of hydrogen for a period of 4 hrs until the hydrogen uptake is complete. The reaction mixture is cooled to room temperature and filtrated over a pad of Celite. The methanol is removed under reduced pressure and replaced with toluene (100 ml). The resulting organic solution is extracted with aqueous HCl (2N, 2×50 ml). The aqueous layer is treated with concentrated aqueous NaOH (30%) to set the pH to 12 and is back-extracted with toluene (2×50 ml). The combined organic layers are concentrated in vacuo to give 12.9 g (85%) of 4-(4-methyl-piperazin-1-ylmethyl)-benzoic acid methyl ester as a pale yellow oil which may be further purified by distillation under reduced pressure.

EXAMPLE 2A

Preparation of N-(4-Methyl-3-nitro-phenyl)-4-(4-methyl-piperazin-1-ylmethyl)-benzamide A solution of trimethylaluminium (2M in toluene, 1.3 ml, 2.6 mmol) is added over a period of 5 min to a solution of 3-nitro-4-methyl-aniline (152 mg, 1.00 mmol) and 4-(4-methyl-piperazin-1-ylmethyl)-benzoic acid methyl ester (248 mg, 1.00 mmol) in toluene (3.0 ml) at 45° C. under an atmosphere of argon. After gas evolution ceases, the dark brown reaction mixture is stirred 30 min before being cooled to 0° C. An aqueous saturated solution of potassium-sodium tartrate (20 ml), t-butyl methyl ether (15 ml) and methylene chloride (10 ml) are added sequentially. The organic phase is separated and washed with aqueous saturated NaHCO$_3$ (10 ml) and aqueous saturated NaCl (10 ml). The aqueous phases are back-extracted with t-butyl methyl, ether (2×15 ml). The organic phases are combined, dried over MgSO$_4$ and concentrated in vacuo to give 383 mg (96 area % by HPLC) of the title compound as pale yellow crystals.

EXAMPLE 2B

Preparation of N-(4-Methyl-3-nitro-phenyl)-4-(4-methyl-piperazin-1-ylmethyl)-benzamide To a solution of 10.95 g (72 mmol) of 3-nitro-4-methyl-aniline in 80 ml of toluene is added a solution of triisobutylaluminium (28% in hexane), 66.5 ml (61 mmol) over a period of 30 min at 0° C. followed by the addition of a solution of 4-(4-methyl-piperazin-1-ylmethyl)-benzoic acid methyl ester (14.9 g, 60 mmol) in toluene (30 ml) during 1 hour at 0° C. under an atmosphere of argon. After stirring for 12 h at room temperature an other portion of triisobutylaluminium (66.5 ml 61 mmol) is added to the dark brown reaction mixture. The mixture is stirred for additional 6 h, then 2 additional small portions of triisobutylaluminium (each 18 ml, 18 mmol) are added and stirring is continued for several hours at room temperature. After acidic and basic workup with sulfuric acid and NaOH the combined organic toluene phases are evaporated in vacuo to give a brown crude product which was crystallized from t-butyl methyl ether to give the title compound as brownish yellow crystals: first crop (11.65 g), sec. crop (3.8 g) and a third crop (1.2 g). in summary 16.65 g (75.3%).

EXAMPLE 2C

Preparation of N-(4-methyl-3-nitro-phenyl)-4-(4-methyl-piperazin-1-ylmethyl)-benzamide 4-methyl-3-nitroaniline (30.0 g, 0.197 mol) is added to a mixture of tetrahydrofuran (120 ml) and N-ethyl-N,N-diisopropyl-amine at 23-25° C. over a period of 5 to 10 min. To this solution chloromethyl-benzoylchloride (38.4 g, 0.20 mol) dissolved in tetrahydrofuran (35 ml) is added over a period of 60-65 min maintaining a temperature of 25-30° C. The reaction mixture is stirred at this temperature for 30 min and then added to N-methylpiperazine (138.2 g, 1.38 mol) over a period of 60 to 90° C. maintaining a temperature of 25-30° C. The resulting suspension is stirred at this temperature for 60 min. Tetrahydrofurane is distilled of at 50° C. under reduced pressure. At the end of the distillation the temperature is adjusted to 45-48° C. and water (300 ml) is added over a period of 45-60 min at this temperature. The resulting suspension is cooled to 23° C. and stirred for 60 min. The suspension is filtered, the filtercake washed with water (225 ml) and dried in vacuo to give 69.2 g of the title compound (95% of theory) as an of-white powder (99.5% area by HPLC).

Alternatively the intermediate N-(4-methyl-3-nitro-phenyl)-4-chloromethyl-benzamide can be isolated by distilling of half of the tetrahydrofuran under reduced pressure and adding the residue to water (300 ml) at a temperature of 20-25° C. over a period of 30 min. After stirring for another 30 min at 0-5° C., the suspension is filtered, washed with water (200 ml) and dried in vacuo. The intermediate is dissolved in tetrahydrofuran (150 ml) and added to N-methylpiperazine (138.2 g, 1.38 mol) over a period of 60 to 90 min maintaining a temperature of 25-30° C. The title compound can be isolated following the above described procedure.

EXAMPLE 3

Preparation of N-(4-Methyl-3-trifluoroacetimidate-phenyl)-4-(4-methyl-piperazin-1-ylmethyl)-benzamide A solution of trimethylaluminium (2M in toluene, 1.25 ml, 2.5 mmol) is added over a period of 5 min to a solution of 3-trifluoroacetimidate-4-methyl-aniline (218 mg, 1.00 mmol) and 4-(4-methyl-piperazin-1-ylmethyl)-benzoic acid methyl ester (248 mg, 1.00 mmol) in toluene (3.0 ml) at 0° C. under an atmosphere of argon. After gas evolution ceases, the dark brown reaction mixture is stirred 3 hrs at 23° C. before being cooled to 0° C. An aqueous saturated solution of potassium-sodium tartrate (20 ml) and t-butyl methyl ether (40 ml) are added sequentially. The organic phase is separated and washed with aqueous saturated NaHCO$_3$ (20 ml) and aqueous saturated NaCl (20 ml). The aqueous phases are back-extracted with t-butyl methyl ether (2×20 ml). The organic phases are combined, dried over MgSO$_4$ and concentrated in vacuo to give 458 mg (94 area % by HPLC) of the title compound as white crystals.

EXAMPLE 4

Preparation of N-(3-amino-4-methyl-phenyl)-4-(4-methyl-piperazin-1-ylmethyl)-benzamide A solution of AlCl$_3$ (1000 mg, 7.5 mmol) in toluene (3 ml) and acetonitrile (3.0 ml) at 0° C. under an atmosphere of argon is treated dropwise with a solution of 3-amino-4-methyl-aniline (470 mg, 6.0 mmol) in toluene (6 ml). The resulting brown solution is heated at 40° C. A solution of 4-(4-methyl-piperazin-1-ylmethyl)-benzoic acid methyl ester (745 mg, 3.0 mmol) in toluene (2 ml) is then added dropwise over a period of 30 min. The resulting mixture is stirred at 40° C. for 8 hrs and then cooled at 0° C. An aqueous saturated potassium-sodium tartrate (30 ml) and aqueous saturated NaHCO$_3$ (40 ml) and t-butyl methyl ether (60 ml) are added sequentially. The organic phase is separated and washed with aqueous saturated NaCl. The aqueous phases are back-extracted with t-butyl methyl ether. The organic phases are combined, dried over MgSO$_4$ and concentrated in vacuo. Purification by flash-chromatography (SiO$_2$, CH$_2$Cl$_2$/MeOH 90:10+1% aq. NH$_3$) gives 825 mg of the title compound (75%) as yellowish crystals.

EXAMPLE 5

Preparation of N-(4-methyl-3-nitro-phenyl)-4-(4-methyl-piperazin-1-ylmethyl)-benzamide Thionyl chloride (53.3 g, 448 mmol) is added over a period of 15 min to a suspension of 4-(4-methyl-piperazin-1-ylmethyl)-benzoic acid (70.0 g, 299 mmol) in toluene (300 ml) at 0° C. At the end of the addition, the reaction mixture is heated at 23° C. over a period of 45 min. The excess of SOCl$_2$ is removed by co-distillation with toluene under reduced pressure at 40° C. At the end of the distillation, the resulting suspension id cooled down to 0° C. and the benzoyl chloride is filtered off, washed with toluene (2×50 ml) and dried in vacuo at 45° C. overnight. Yield: 55.0 g, 79% of theory based on the di-hydrochloride salt of the benzoylchloride, white solid. The dried benzoyl chloride (55 g) is then resuspended in toluene (100 ml). A solution of 4-methyl-3-nitroaniline (22.75 g, 145 mmol) and pyridine (34.4 g, 435 mmol) in toluene (60 ml) is added dropwise at 23° C. over a period of 15 min. The resulting orange-brown reaction mixture is heated at 45° C. and is stirred for 6 hrs. The suspension is filtrated and the filtercake is washed successively with toluene (300 ml) and acetone (350 ml), and is then suspended in water (350 ml). Aqueous NaOH (30%) is added until the pH of the suspension reaches 11 and remains stable. The suspension is further stirred for 1 h at 40° C. before being filtrated. The filtercake is washed with water (5×50 ml) and dried in vacuo to give 51.3 g of the title compound (96%) as beige crystals, (98.7% area by HPLC).

Preparation of 4-(4-methyl-piperazin-1-ylmethyl)-benzoic acid:

A suspension of 4-formyl-benzoic acid (10.0 g, 67 mmol) in methanol (100 ml) is treated sequentially with 1-methylpiperazine (7.3 g, 73 mmol) and platinum (5%) on sulfided carbon (1 g). The resulting suspension is then heated at 80° C. and is subjected to a pressure of 5 bar of hydrogen for a period of 20 hrs until the hydrogen uptake is complete. The reaction mixture is cooled to room temperature and filtrated over a pad of Celite. Water (20 ml) is used to rinse the reactor and dissolve the fraction of 4-(4-methyl-piperazin-1-ylmethyl)-benzoic acid that crystallizes on the walls during the cooling of the reaction mixture. The resulting aqueous solution is filtrated over the pad of Celite employed previously. The combined filtrates are concentrated in vacuo and crystallized in EtOH/H$_2$O 9:1 v/v to give 10.9 g (70%) of 4-(4-methyl-piperazin-1-ylmethyl)-benzoic acid as colorless crystals.

EXAMPLE 6

Preparation of N-(3-guanidino-4-methyl-phenyl)-4-(4-methyl-piperazin-1-ylmethyl)-benz-amide In analogous manner to Example 4, 3-guanidino-4-methyl-aniline (2.51 g, 11.5 mmol) and 4-(4-methyl-piperazin-1-ylmethyl)-benzoic acid (70.0 g, 299 mmol) in toluene (300 ml) in the presence of thionyl chloride (53.3 g, 448 mmol) give 12.1 g (89%) of the title compound as pale colorless crystals.

EXAMPLE 7

Preparation of 4-dichloromethyl-N-[4-methyl-3-(4-pyridin-3-yl-pyrimidin-2-ylamino)-phenyl]-benzamide To a suspension of 4-methyl-N*3*-(4-pyridin-3-yl-pyrimidin-2-yl)-benzene-1,3-diamine (2.00 g mg, 7.21 mmol) in toluene (22 ml) at 45° C. under an atmosphere of argon is added sequentially 4-dichloromethyl-benzoic acid methyl ester (1.90 g, 8.67 mmol) and AlMe$_3$ (2 M in toluene, 12.6 ml, 25.2 mmol). The resulting brown solution is stirred at 45° C. for a period of 3.5 hrs. The reaction mixture is then cooled to 0° C. and quenched by slow addition of a saturated aqueous solution of Rochelle salt (70 ml) which causes the precipitation of the crude product. t-Butyl methyl ether (150 ml) and methylene chloride (100 ml) are added sequentially to the suspension which are then washed with aqueous saturated NaHCO$_3$ (100 ml) and aqueous saturated NaCl (100 ml). The aqueous phases are back-extracted with t-butyl methyl ether (100 ml). The crude product, which is contained in the combined organic phases, is filtered off with suction, washed with t-butyl methyl ether and dried in vacuo. Yield: 3.35 g of the title compound, 84% of theory, as beige crystals, (HPLC: 91% area).

EXAMPLE 8

Preparation of N-(3-guanidino-4-methyl-phenyl)-4-(4-methyl-piperazin-1-ylmethyl)-benz-amide In analogous manner to Example 4, 3-guanidino-4-methyl-aniline (1.00 g, 6.09 mmol) and 4-(4-methyl-piperazin-1-ylmethyl)-benzoic acid methyl ester (1.50 g, 6.04 mmol) in toluene (22 ml) and acetonitrile (6 ml) in the presence of AlCl$_3$ (2.0 g, 15.0 mmol) at 40° C. give 1.26 g (55%) of the title compound as pale colorless crystals.

EXAMPLE 9

Preparation of 4-(4-methyl-piperazin-1-ylmethyl)-N-[4-methyl-3-(4-pyridin-3-yl-pyrimidin-2-ylamino)-phenyl]-benzamide A suspension of N-(3-guanidino-4-methyl-phenyl)-4-(4-methyl-piperazin-1-ylmethyl)-benz-amide (30 g, 79 mmol) in n-butanol (150 ml) at 120° C. under an atmosphere of nitrogen is treated with 3-dimethylamino-1-pyridin-3-yl-propenone (15.3 g, 87 mmol). The resulting suspension is heated at 150° C. for 5 hrs. The reaction mixtures becomes a homogeneous deep orange solution and dimethylamine is removed by the distillation of n-butanol (130 ml). n-Butanol (20 ml) is added during the distillation. Butyl acetate (60 ml) is added dropwise at 100° C. and the solution is cooled to 0° C. within 1 hr and stirred at 0° C. for 16 hrs. The resulting deep orange suspension is filtered off with suction, the isolated solid is washed with n-butanol (2×50 ml) and water (2×50 ml) and dried in vacuo at 60° C. Yield: 36.4 g of the title compound, 93% based on theory, as off-white crystals. (99.6% area by HPLC).

EXAMPLE 10

Preparation of 4-(4-methyl-piperazin-1-ylmethyl)-N-[4-methyl-3-(4-pyridin-3-yl-pyrimidin-2-ylamino)-phenyl]-benzamide To a mixture of 4-(3-pyridyl)-2-pyrimidine-amine (172.2 mg, 1.0 mmol), N-(3-bromo-4-methyl-phenyl)-4-(4-methyl-piperazin-1-ylmethyl)-benzamide (402.4 mg, 1.0 mmol) and sodium tert.-butylate (144.2 mg, 1.5 mmol) is added a mixture of rac-BINAP (31.2 mg, 0.050 mmol) and $Pd_2(dba)_3$*$CHCl_3$ (13 mg, 0.013 mmol) under argon. After addition of 3 ml of xylene the suspension is sonicated for 10 minutes then stirred for 5 hours under reflux. After cooling to room temperature, water (10 ml) is added to the dark brown oil and the product extracted 4 times with methylene chloride (10 ml each). The combined organic extracts are dried over $MgSO_4$ and concentrated in vacuo. The brown oil is purified by flash-chromatography ($SiO_2$, methanol). The product, a pale yellow solid is dissolved in methylene chloride, filtered and concentrated in vacuo. Yield: 484.3 mg of the title compound, 72% of theory, (99.9% area by HPLC). The product contains typically roughly 10% of isomers which can be eliminated by preparative reversed phase chromatography.

EXAMPLE 11

Preparation of N-(3-amino-4-methyl-phenyl)-4-(4-methyl-piperazin-1-ylmethyl)-benzamide A solution of N-(4-methyl-3-nitro-phenyl)-4-(4-methyl-piperazin-1-ylmethyl)-benzamide (100 g, 260 mmol) in n-butanol (1 l) is treated with platinum (5%) on carbon (1.0 g). The resulting suspension is then heated to 70° C. and hydrogen is applied with a pressure of 0.2 bar for a period of 6 h until the hydrogen uptake is complete. The reaction mixture is cooled to room temperature and filtrated. n-Butanol is used to wash the catalyst. This solution is suitable for example 12. For isolation of the product is reduced to a third and crystallized by cooling down to 0° C. (HPLC: 98.0% area).

Alternatively a solution of N-(4-methyl-3-nitro-phenyl)-4-(4-methyl-piperazin-1-ylmethyl)-benzamide (60 g, 163 mmol) in ethanol 90% (300 ml) at room temperature under an atmosphere of nitrogen is treated sequentially with platinum (5%) on carbon (6.0 g) and potassium formate (68.5 g, 814 mmol). The resulting suspension is then heated at 80° C. for a period of 16 hrs. The reaction mixture is filtrated at 70° C. over a pad of Celite. Ethanol 90% (150 ml) and water (150 ml) are used to rinse the reactor. Ethanol is removed from the combined filtrates by distillation in vacuo at an external temperature 60° C. The crude product separates from the aqueous concentrate as an oil during the distillation, crystallizes upon subsequent cooling to 23° C. within 2 hrs and is filtered of with suction, washed with ethanol (200 ml) and dried in vacuo. Yield: 55 g of the title compound, 99% of theory, as yellowish crystals. (HPLC: 98.0% area).

EXAMPLE 12

Preparation of N-(3-guanidino-4-methyl-phenyl)-4-(4-methyl-piperazin-1-ylmethyl)-benz-amide A suspension of N-(3-amino-4-methyl-phenyl)-4-(4-methyl-piperazin-1-ylmethyl)-benzamide (50 g, 144 mmol) in n-butanol (300 ml) at 85° C. is treated sequentially with concentrated aqueous HCl until the pH reaches 2.5 (HCl 37%, 35 g) and with a solution of cyanamide (12.1 g, 288 mmol) in water (12 ml) over a period of 30 min. The resulting reaction mixture is stirred at 85° C. for 20 hrs during which time the starting material dissolves and the desired product crystallizes out of solution as the di-hydrochloride salt. Concentrated HCl (37%, 6.3 g) is added during the reaction to maintain the pH at 2.5. The reaction mixture is then allowed to cool down to room temperature within 1.5 hrs. The product is filtered off with suction, washed with n-butanol (3×50 ml) and dried in vacuo at 60° C. Yield 60.7 g of the di-hydrochloride salt, 93% of theory (99% area by HPLC).

The di-hydrochloride salt is dissolved in water (250 ml) at 35° C. An aqueous solution of NaOH (2N, 150 ml) is added and the pH of the solution increases to 13.2. The desired product separates from the aqueous solution as an oil which crystallizes upon cooling to 0° C. After 1 hr stirring at 0° C., the product is filtered off, washed with an aqueous solution of $K_2CO_3$ (5.5 g/L, 2×50 ml) and dried in vacuo at 50° C. Yield: 41.2 g of the title compound, 89% of theory based on the intermediate di-hydrochloride salt, as beige crystals, (98.7% area by HPLC).

The invention claimed is:

1. A pharmaceutical composition comprising,
   a) one or more pharmaceutically acceptable excipients, and
   b) at least one pharmaceutically active compound of formula IV

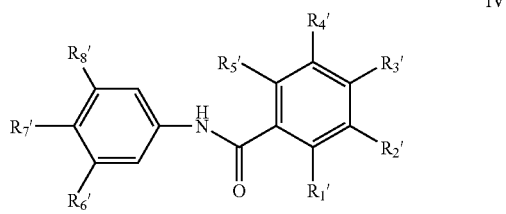

$R_3'$ is (4-methyl-piperazinyl)-methyl and $R_1'$, $R_2'$, $R_4'$ and $R_5'$ are independently hydrogen, cyano; lower alkyl; hydroxy- or amino-substituted lower alkyl; trifluoromethyl; free, etherified or esterified hydroxy; lower alkoxy; lower alkanoyloxy; free, alkylated or acylated amino; mono- or di-lower alkylamino; lower alkanoylamino; benzoylamino; free or esterified carboxy; lower alkoxycarbonyl and halogen;

$R_6$ is halogen, $NH_2$, $NO_2$, $NHC(O)CF_3$, $NHC(O)CH_3$, or $NHC(NH)NH_2$, $R_7$ is methyl and $R_8$ is hydrogen;

and one of the radicals $R_6'$, $R_7'$ and $R_8'$ is

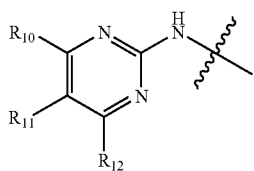

wherein $R_{10}$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, and $R_{11}$ and $R_{12}$ are each independently of the other hydrogen or lower alkyl and the other two radicals are hydrogen, lower alkyl, benzyl or phenyl, or a pharmaceutically acceptable salt or crystal form thereof; and c) between 0.00001% and 5% by weight of at least one compound of formula I

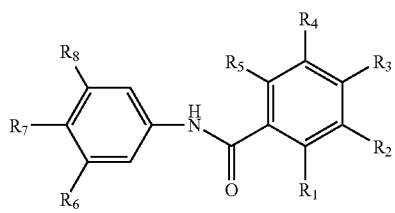

I wherein $R_3$ is (4-methyl-piperazinyl)-methyl and $R_1$, $R_2$, $R_4$ and $R_5$ are independently hydrogen, cyano; lower alkyl; hydroxy- or amino-substituted lower alkyl; trifluoromethyl; free, etherified or esterified hydroxy; lower alkoxy; lower alkanoytoxy; free, alkylated or acylated amino; mono- or di-lower alkylamino; lower alkanoylamino; benzoylamino; free or esterified carboxy; lower alkoxycarbonyl and halogen;

$R_6$ is halogen, $NH_2$, $NO_2$, $NHC(O)CF_3$, $NHC(O)CH_3$, or $NHC(NH)NH_2$, $R_7$ is methyl and $R_8$ is hydrogen;

or a salt or crystal form thereof.

2. A pharmaceutical composition according to claim 1, wherein b) is (4-[(4-methyl-1-piperazin-1-ylmethyl)-N-[4-methyl-3-[4-(3-pyridinyl)-2-pyrimidinyl]amino]phenyl]benzamide) or a pharmaceutically acceptable salt or crystal form thereof, and c) is at least one compound of formula I wherein, $R_3$ is (4-methyl-piperazinyl)-methyl, $R_1$, $R_2$, $R_4$, $R_5$ and $R_8$ are hydrogen, $R_6$ is halogen, $NH_2$, $NO_2$, $NHC(O)CF_3$, $NHC(O)CH_3$ or $NHC(NH)NH_2$, and $R_7$ is methyl, or a salt or crystal form thereof.

3. A pharmaceutical composition according to claim 2 which comprises between 0.00001% and 0.1% by weight of the compound of formula I.

* * * * *